United States Patent
Gou et al.

(10) Patent No.: US 11,493,447 B2
(45) Date of Patent: Nov. 8, 2022

(54) METHOD FOR REMOVING BACKGROUND FROM SPECTROGRAM, METHOD OF IDENTIFYING SUBSTANCES THROUGH RAMAN SPECTROGRAM, AND ELECTRONIC APPARATUS

(71) Applicant: Nuctech Company Limited, Beijing (CN)

(72) Inventors: Wei Gou, Beijing (CN); Hongqiu Wang, Beijing (CN); Huacheng Feng, Beijing (CN)

(73) Assignee: Nuctech Company Limited, Beijing (CN)

( * ) Notice: Subject to any disclaimer, the term of this patent is extended or adjusted under 35 U.S.C. 154(b) by 775 days.

(21) Appl. No.: 16/473,495

(22) PCT Filed: Nov. 17, 2017

(86) PCT No.: PCT/CN2017/111588
§ 371 (c)(1),
(2) Date: Jun. 25, 2019

(87) PCT Pub. No.: WO2018/121121
PCT Pub. Date: Jul. 5, 2018

(65) Prior Publication Data
US 2019/0339205 A1    Nov. 7, 2019

(30) Foreign Application Priority Data
Dec. 26, 2016    (CN) .......................... 201611222587.6

(51) Int. Cl.
*G01J 3/44* (2006.01)
*G01N 21/65* (2006.01)
(Continued)

(52) U.S. Cl.
CPC ............ *G01N 21/65* (2013.01); *A61B 5/0075* (2013.01); *G01J 3/02* (2013.01); *G01J 3/44* (2013.01); *G01N 2201/129* (2013.01)

(58) Field of Classification Search
CPC ............. G01N 21/65; G01N 2201/129; G01N 21/274; G01N 23/223; G01J 3/44;
(Continued)

(56) References Cited

U.S. PATENT DOCUMENTS

2009/0012403 A1*    1/2009    Carron ................... G16H 30/40
600/476

FOREIGN PATENT DOCUMENTS

| CN | 101017143 A | 8/2007 |
| CN | 103955518 A | 7/2014 |

(Continued)

OTHER PUBLICATIONS

"Chinese Application Serial No. 201611222587.6, Office Action dated Apr. 20, 2020", w/ English Translation, (Apr. 20, 2020), 20 pgs.

(Continued)

*Primary Examiner* — Abdullahi Nur
(74) *Attorney, Agent, or Firm* — Schwegman Lundberg & Woessner, P.A.

(57) ABSTRACT

The disclosure provides a method for removing background from a spectrogram, including: finding out peak information of a raw spectrogram, the peak information including a peak position, a starting point, an ending point, and a peak width w of a peak; processing, within each peak area defined by the starting point and the ending point of each peak of the raw spectrogram, each peak of the raw spectrogram by using a SNIP method so as to obtain background data within each peak area; replacing, within each peak area, data of the raw spectrogram with the background data obtained through
(Continued)

processing by using the SNIP method, so as to form a background spectrogram in a fitting way; smoothing the formed background spectrogram; and subtracting the smoothed background spectrogram from the raw spectrogram so as to obtain a spectrogram with removed background.

11 Claims, 7 Drawing Sheets

(51) Int. Cl.
*G01J 3/02* (2006.01)
*A61B 5/00* (2006.01)

(58) Field of Classification Search
CPC .... G01J 2003/4424; G06F 16/00; G06K 9/00; G06K 9/0053; G06K 9/00543
See application file for complete search history.

(56) References Cited

FOREIGN PATENT DOCUMENTS

| JP | 3711207 B2 | 8/2005 |
|---|---|---|
| WO | WO-2014094039 A1 | 6/2014 |

OTHER PUBLICATIONS

"European Application Serial No. 17886286.8, Extended European Search Report dated Jun. 19, 2020", (dated Jun. 9, 2020), 9 pgs.

Bocklitz, Thomas, et al., "How to pre-process Raman spectra for reliable and stable models?", Analytica chimica acta 704.1-2, (Jun. 21, 2011), 47-56.

Guo, Shuxia, et al., "Optimization of Raman-spectrum baseline correction in biological application", Analyst 141.8, (Jan. 1, 2016), 2396-2404.

Robinson, Mark D., et al., "A dynamic programming approach for the alignment of signal peaks in multiple gas chromatography-mass spectrometry experiments", BMC bioinformatics 8.1, (Oct. 29, 2007), 1-14.

Ryan, C. G., et al., "SNIP, a statistics-sensitive background treatment for the quantitative analysis of PIXE spectra in geoscience applications", Nuclear Instruments and Methods in Physics Research Section B: Beam Interactions with Materials and Atoms 34.3, (1988), 396-402.

Tomoyori, K., et al., "Background elimination using the SNIP algorithm for Bragg reflections from a protein crystal measured by a TOF single-crystal neutron diffractometer", Journal of Physics: Conference Series. vol. 664. No. 7. IOP Publishing, (Oct. 23, 2015), 7 pgs.

"International Application Serial No. PCT/CN2017/111588, International Search Report dated Feb. 14, 2018", (dated Feb. 14, 2019), 3 pgs.

"International Application Serial No. PCT/CN2017/111588, Written Opinion dated Feb. 14, 2018", (Feb. 14, 2018), 4 pgs.

Long, Bin, et al., "A self-adaptive method for the clipping of scatter background of ? spectrum", Nuclear Electronics and Detection Technology 33.10, (Oct. 20, 2013), 1293-1296.

Yin, Wangming, et al., "Discussion and Application of Eliminating the Background in ?-ray Spectrum by SNIP Algorithm", Journal of East China Geological Institute 32.3, (Sep. 30, 2009), 245-248.

\* cited by examiner

METHOD FOR REMOVING BACKGROUND FROM SPECTROGRAM, METHOD OF IDENTIFYING SUBSTANCES THROUGH RAMAN SPECTROGRAM, AND ELECTRONIC APPARATUS

PRIORITY APPLICATIONS

This application is a U.S. National Stage Filing under 35 U.S.C. 371 from International Application No. PCT/CN2017/111588, filed on Nov. 17, 2017, and published as WO2018/121121 on Jul. 5, 2018, which claims the benefit of priority to Chinese Application No. 201611222587.6, filed on Dec. 26, 2016; the benefit of priority of each of which is hereby claimed herein, and which applications and publication are hereby incorporated herein by reference in their entirety.

FIELD OF THE DISCLOSURE

Embodiments of the present disclosure generally relate to the field of spectrum analyzing and processing technologies, and in particular to a method for removing background from a spectrogram, a method of identifying substances through a Raman spectrogram, and an electronic apparatus.

DESCRIPTION OF THE RELATED ART

Raman spectrum is a molecular vibration spectrum that can reflect the fingerprint characteristics of molecules, and can be used for the inspection of substance. Raman spectrum detection can inspect and identify the substance by the Raman spectrum generated from the Raman scattering effect of the object to be inspected with respect to exciting light. Raman spectrum detection technology has been widely used in the fields of liquid detection, jewelry detection, explosive detection, drug detection, pesticide detection and the like.

When analyzing and processing a spectrogram of the Raman spectrum, a problem to be often faced is how to effectively and quickly remove background from the Raman spectrogram to obtain data of peaks corresponding to components of substance, in order to facilitate subsequent processing.

An existing conventional method for removing the background includes processing the spectrogram by using a least square method with a penalty function. However, when removing the background by using the least square method with a penalty function, a longer time will be required, setting of parameters is complex, improper setting of parameters may result in poor effect of removing the background, or even adversely affecting final effect of removing the background.

SUMMARY

According to an aspect of the present disclosure, there is provided a method for removing background from a spectrogram, comprising:

finding out peak information of a raw spectrogram, the peak information including a peak position, a starting point, an ending point, and a peak width of a peak;

processing, within each peak area defined by the starting point and the ending point of each peak of the raw spectrogram, each peak of the raw spectrogram by using a SNIP method so as to obtain background data within each peak area;

replacing, within each peak area, data of the raw spectrogram with the background data obtained through processing by using the SNIP method, so as to form a background spectrogram in a fitting way;

smoothing the formed background spectrogram; and subtracting the smoothed background spectrogram from the raw spectrogram so as to obtain a spectrogram with removed background.

According to an aspect of the present disclosure, there is provided a method for removing background from a spectrogram, comprising steps of:

finding out peak information of a raw spectrogram, the peak information including a peak position, a starting point, an ending point, and a peak width of a peak;

processing, within each peak area defined by the starting point and the ending point of each peak of the raw spectrogram, each peak of the raw spectrogram by using a SNIP method so as to obtain background data within each peak area;

replacing, within each peak area, data of the raw spectrogram with the background data obtained through processing by using the SNIP method, so as to form a background spectrogram in a fitting way;

smoothing the formed background spectrogram; and subtracting the smoothed background spectrogram from the raw spectrogram so as to obtain a spectrogram with removed background.

According to some embodiments, the step of obtaining background data within each peak area comprises:

transforming, within each peak area, an intensity value corresponding to each wave number within the peak area by using a transformation formula, the transformation formula being: $v(i)=\ln[\ln(\sqrt{y(i)+1}+1)+1]$;

performing iteration calculation based on a SNIP formula so as to successively calculate $v_1(i)$, $v_2(i)$, unit $v_m(i)$, the SNIP formula being: $v_p(i)=\min\{v_{p-1}(i),[v_{p-1}(i+p)+v_{p-1}(i-p)]/2\}$; and performing, after calculating $v_m(i)$, an inverse operation based on the above transformation formula to calculate $y(i)$ corresponding to $v_m(i)$ so as to obtain the background data within the peak area, wherein, i is a wave number of the raw spectrogram, $y(i)$ is an intensity value corresponding to the $i^{th}$ wave number of the raw spectrogram, and $v(i)$ is an operation result of $y(i)$;

wherein, m is a predetermined number of iterations, p is a current number of iterations, $1 < p \leq m$, $v_p(i)$ represents $v(i)$ calculated through the $p^{th}$ iteration, $v_{p-1}(i)$, $v_{p-1}(i+p)$ and $v_{p-1}(i-p)$ respectively represent $v(i)$, $v(i+p)$ and $v(i-p)$ calculated through the $(p-1)^{th}$ iteration, and $v(i+p)$ and $v(i-p)$ respectively represent operation results of intensity values corresponding to the $(i+p)^{th}$ wave number and the $(i-p)^{th}$ wave number.

According to some embodiments, for each peak area, the predetermined number of iterations m meets a following relation:

$m=(w-1)/2$, where w is the peak width of the peak area.

According to another aspect of the present disclosure, there is further provided a method of identifying substances through a Raman spectrogram, comprising:

a standard spectrogram library establishing step: measuring Raman spectrums of a plurality of samples so as to obtain standard spectrograms of the plurality of samples, preprocessing the standard spectrograms and extracting peak information of the standard spectrograms including peak intensities, peak positions, peak areas and peak widths, and storing the pre-processed standard spectrograms and the extracted peak information into a data base so as to establish a standard spectrogram library;

a measured spectrogram obtaining step: measuring a Raman spectrum of a substance to be detected so as to obtain a measured spectrogram;

a measured spectrogram preprocessing and peak information extracting step: preprocessing the measured spectrogram and extracting peak information of the measured spectrogram, the peak information including a peak intensity, a peak position, a peak area and a peak width of the measured spectrogram;

a peak matching step: comparing the peak information of the measured spectrogram and the peak information of the standard spectrograms, so as to screen and select the standard spectrogram having the peak information matching the peak information of the measured spectrogram; and identification step: comparing in correlation between data of the measured spectrogram and data of the standard spectrogram selected in the above peak matching step, to screen and select the standard spectrogram most associated with the measured spectrogram so as to identify the detected substance, wherein, the preprocessing the measured spectrogram in the measured spectrogram preprocessing and peak information extracting step comprises: removing background from the measured spectrogram by using the method described in any one of embodiments of the present disclosure.

According to some embodiments, the preprocessing the standard spectrograms in the standard spectrogram library establishing step comprises: removing background from the standard spectrograms by using the method described in any one of embodiments of the present disclosure.

According to some embodiments, the peak matching step comprises:

an ordering step: ordering, with the greatest in front in accordance with peak intensities, peaks of the measured spectrogram and peaks of the standard spectrograms respectively, so as to select ordered first N peaks of the measured spectrogram and the standard spectrograms; and a first matching step: comparing peak position information of the ordered first N peaks of the measured spectrogram and the standard spectrograms, so as to screen and select the standard spectrogram having the peak information matching the peak information of the measured spectrogram.

According to some embodiments, the first matching step specifically comprises:

calculating absolute differences between peak positions of ordered first N peaks in accordance with the following formula (1); and determining that the peak information of the measured spectrogram matches the peak information of the standard spectrogram when the calculated absolute differences between the peak positions meets the following condition (1); and determining that the peak information of the measured spectrogram does not match the peak information of the standard spectrogram when the calculated absolute differences between the peak positions do not meet the following condition (1), wherein:

the formula (1) is: $pD=|p2[j].fPos-p1[i].fPos|$, the condition (1) is: $pD<p2[j].fWidth/3$ and $pD<p1[i].fWidth/3$, where, N is a predetermined number of compared peaks, N is a natural number greater than or equal to three;

I and j respectively represent order numbers of the ordered peaks of the standard spectrogram and the measured spectrogram, i and j are each an integer greater than or equal to zero and less than or equal to N;

$p1[i].fPos$ represents a peak position of the $i^{th}$ peak ordered in the standard spectrogram;

$p2[j].fPos$ represents a peak position of the $j^{th}$ peak ordered in the measured spectrogram;

$p1[i].fWidth$ represents a peak width of the $i^{th}$ peak ordered in the standard spectrogram;

$p2[j].fWidth$ represents a peak width of the $j^{th}$ peak ordered in the measured spectrogram; and pD represents an absolute difference between peak positions.

According to some embodiments, the peak matching step further comprises:

a peak matching weight calculation step: establishing a penalty function in accordance with the following formula (2) so as to calculate a peak matching weight; and a second matching step: determining that the peak information of the measured spectrogram matches the peak information of the standard spectrogram when the peak matching weight is greater than or equal to a preset weight threshold; and determining that the peak information of the measured spectrogram does not match the peak information of the standard spectrogram when the peak matching weight is less than or equal to the preset weight threshold, wherein, the formula (2) is:

$$h=(1-2*|j-i|/10)*(0.5/(i+1))*\exp(-pD*2/\min(p1[i].fWidth,p2[j].fWidth)),$$

where, h represents the peak matching weight.

According to some embodiments, the peak matching weight calculation step and the second matching step are performed when determining that the peak information of the measured spectrogram matches the peak information of the standard spectrogram in the first matching step.

According to some embodiments, N is a natural number greater than or equal to three and less than or equal to five.

According to some embodiments, the step of comparing in correlation between data of the measured spectrogram and data of the standard spectrogram selected in the above peak matching step is performed within a union interval of peak areas of all of peaks of the measured spectrogram and the standard spectrogram.

According to a further aspect of the present disclosure, there is also provided an electronic apparatus, comprising:

a storage for storing executable instructions therein; and a processor configured to execute the executable instructions stored in the storage to perform the method described in any one of aspects of embodiments of the present disclosure.

DETAILED DESCRIPTION OF THE EMBODIMENTS

Figure 1:
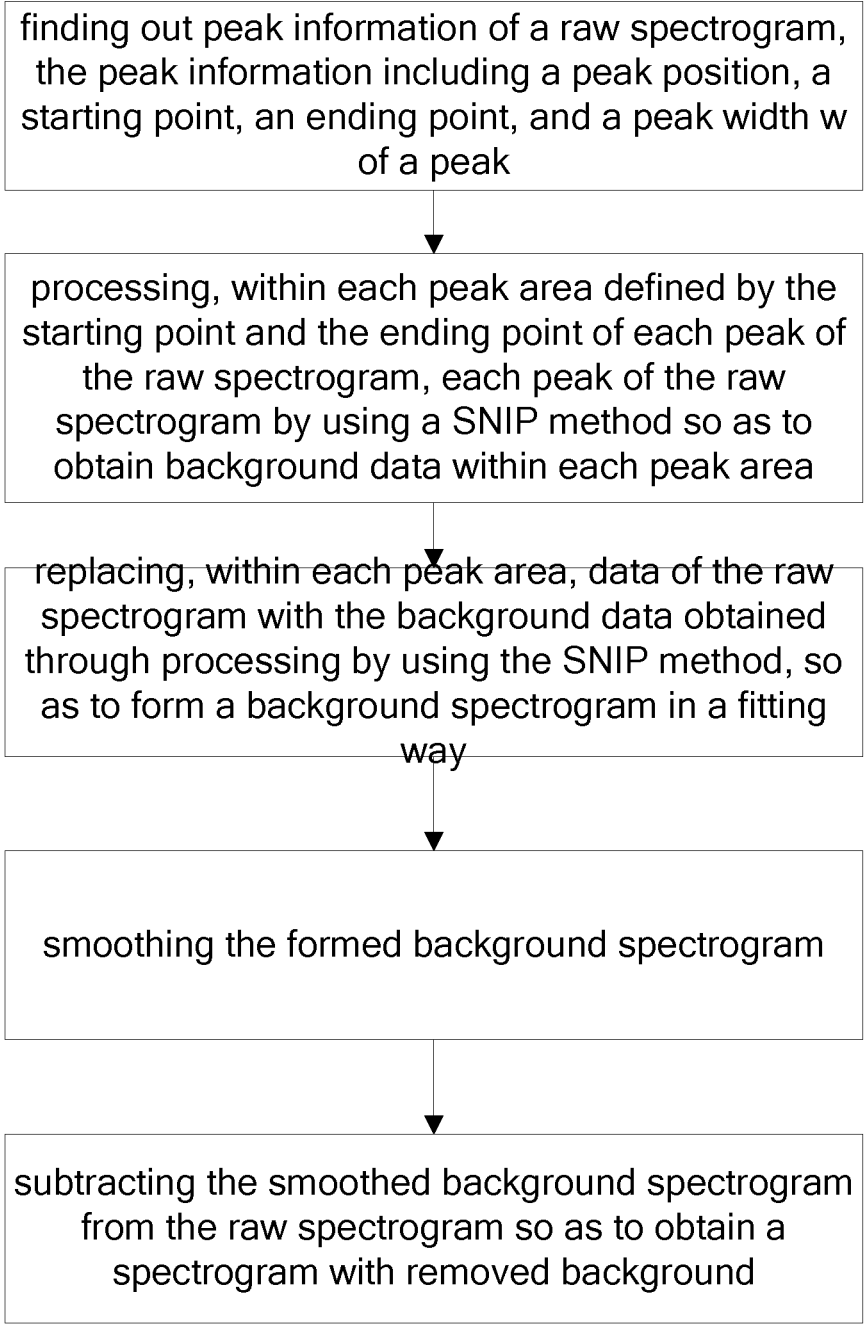
FIG. 1 is a flow chart schematically showing a method for removing background from a spectrogram according to an embodiment of the present disclosure.

Technical solutions of the present disclosure will be described hereinafter in more detail by the way of embodiments with reference to the accompanying drawings. The same or similar reference numerals refer to the same or similar elements throughout the description. The description of the embodiments of the present disclosure made with reference to the accompanying drawings is intended to interpret the general inventive concept of the present disclosure, rather than being construed as a limiting to the present disclosure.

In this text, for purpose of description, phrases such as "first, "second", "A, B, C" and the like are used to describe steps in a method, but unless otherwise specified, such phrases should not be construed as a limiting to a sequence of performing the steps.

In this text, "SNIP" means a Statistics-sensitive Nonlinear Iterative Peak-clipping algorithm.

FIG. 1 schematically shows a method for removing background from a spectrogram according to an exemplary embodiment of the present disclosure. As shown in FIG. 1, the method may comprise following steps:

a peak information searching step: finding out peak information of a raw spectrogram, the peak information including a peak position, a starting point, an ending point, and a peak width w of a peak;

a background data obtaining step: processing, within each peak area defined by the starting point and the ending point of each peak of the raw spectrogram, each peak of the raw spectrogram by using a SNIP method so as to obtain background data within each peak area;

a background spectrogram forming step: replacing, within each peak area, data of the raw spectrogram with the background data obtained through processing by using the SNIP method, so as to form a background spectrogram in a fitting way;

a smoothing step: smoothing the formed background spectrogram; and a background removing step: subtracting the smoothed background spectrogram from the raw spectrogram so as to obtain a spectrogram with removed background.

Hereinafter, a method for removing background from a spectrogram according to embodiments of the present disclosure will be further described in detail by taking a Raman spectrogram as an example and by referring to the accompanying drawings.

Figure 2:
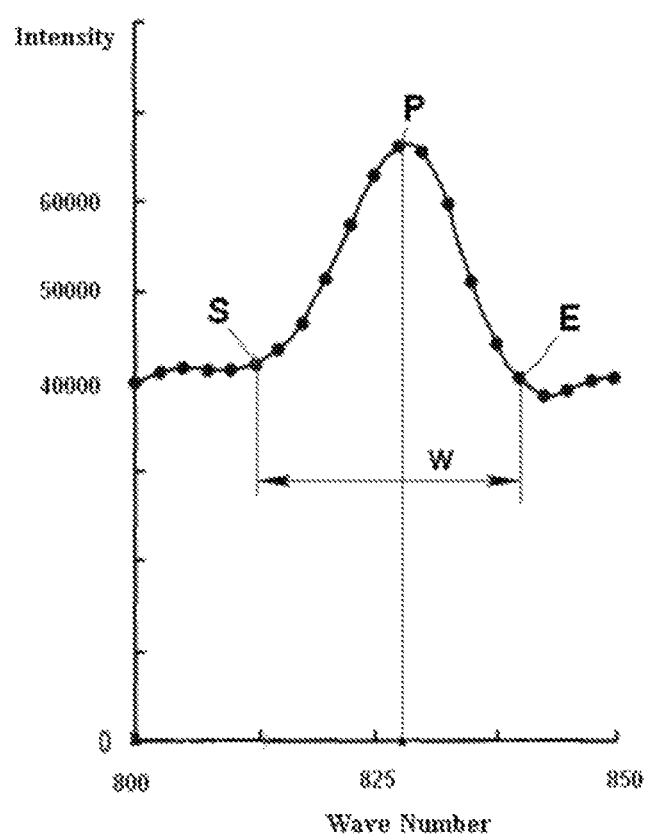
FIG. 2 schematically shows one peak of a Raman spectrogram of a substance.

FIG. 2 schematically shows one peak of a Raman spectrogram of a substance. The peak information of a Raman spectrogram may include a peak position, a starting point, an ending point, a peak width w and a peak intensity of a peak. Generally, the horizontal ordinate of the Raman spectrogram represents a Raman shift or wave number (in unit of $cm^{-1}$), and the longitudinal coordinate represents an intensity (which is dimensionless or represented by a.u.). When performing mathematical calculation, the Raman spectrogram may be regarded as a set of discrete data points, as indicated by black circular dots shown in FIG. 2, where the horizontal ordinate of the data point may be referred to as a wave number, and the longitudinal coordinate may be referred to as an intensity or intensity value. In this way, as shown in FIG. 2, a peak position may be a position where the highest point P of the peak is located, that is, the wave number corresponding to the point P; the starting point and the ending point of the peak may refer to wave numbers corresponding to the starting point S and the ending point E of the peak; the peak width w may be a width defined by the starting point S and the ending point E of the peak, that is, a difference between the wave number of the ending point E and the wave number of the starting point S of the peak.

In an example, the above peak information searching step may be performed to search for a peak by using a simple comparison method. Specifically, among intensities or intensity values of a spectrogram, if the intensity value corresponding to a certain wave number is much greater than intensity values corresponding to several adjacent wave numbers, it may be said that there is a peak at the wave number. Alternatively, the above peak information searching step may be performed to search for a peak by using a derivative method. Specifically, if a spectrogram is regarded as a continuous curve, first, second and third order derivatives of the spectrogram may be calculated. In general, the first order derivative will cross zero at a peak position from positive to negative, the second order derivative will has a negative local minimum at the peak position, and the third order derivative will cross zero at the peak position from negative to positive. Thereby, characteristics of a shape of the spectrogram curve near the peak position are utilized so that the peak information such as the peak position can be determined accurately by means of variation of a slope or curvature of the spectrogram curve.

According to an embodiment of the present disclosure, the above background data obtaining step may further comprises following steps:

transforming, within each peak area, an intensity value corresponding to each wave number within the peak area by using a transformation formula, the transformation formula being: $v(i)=\ln[\ln(\sqrt{y(i)+1}+1)+1]$;

performing iteration calculation based on a SNIP formula so as to successively calculate $v_1(i)$, $v_2(i)$, unit $v_m(i)$, the SNIP formula being:

$$v_p(i)=\min\{v_{p-1}(i),[v_{p-1}(i+p)+v_{p-1}(i-p)]/2\}; \text{ and}$$

performing, after calculating $v_m(i)$, an inverse operation based on the above transformation formula to calculate y(i) corresponding to $v_m(i)$ so as to obtain the background data within the peak area, wherein, i is a wave number of the raw spectrogram, y(i) is an intensity value corresponding to the $i^{th}$ wave number of the raw spectrogram, and v(i) is an operation result of y(i);

m is a predetermined number of iterations, p is a current number of iterations, $1<p\leq m$, $v_p(i)$ represents v(i) calculated through the $p^{th}$ iteration, $v_{p-1}(i)$, $v_{p-1}(i+p)$ and $v_{p-1}(i-p)$ respectively represent v(i), v(i+p) and v(i-p) calculated through the $(p-1)^{th}$ iteration and v(i+p) and v(i-p) respectively represent operation results of intensity values corresponding to the $(i+p)^{th}$ wave number and the $(i-p)^{th}$ wave number.

According to embodiments of the present disclosure, for each peak area, the predetermined number of iterations m meets a relation: m=(w−1)/2, where w is a peak width. In this relation, w is a peak width corresponding to the peak area. Peak widths of respective peak areas may be different from each other, thus the predetermined number of iterations m may be different for the respective peak area. Thereby, by determining the predetermined numbers of iterations based on the peak widths of respective peak areas, the background of respective peaks may be fitted adaptively, and meanwhile, the calculation speed can be improved.

In an example, the above smoothing step may include smoothing operation by using method such as a least square moving smoothing method, a Gaussian filter smoothing method, a median filtering or mean filtering smoothing method, or the like.

Figure 3:
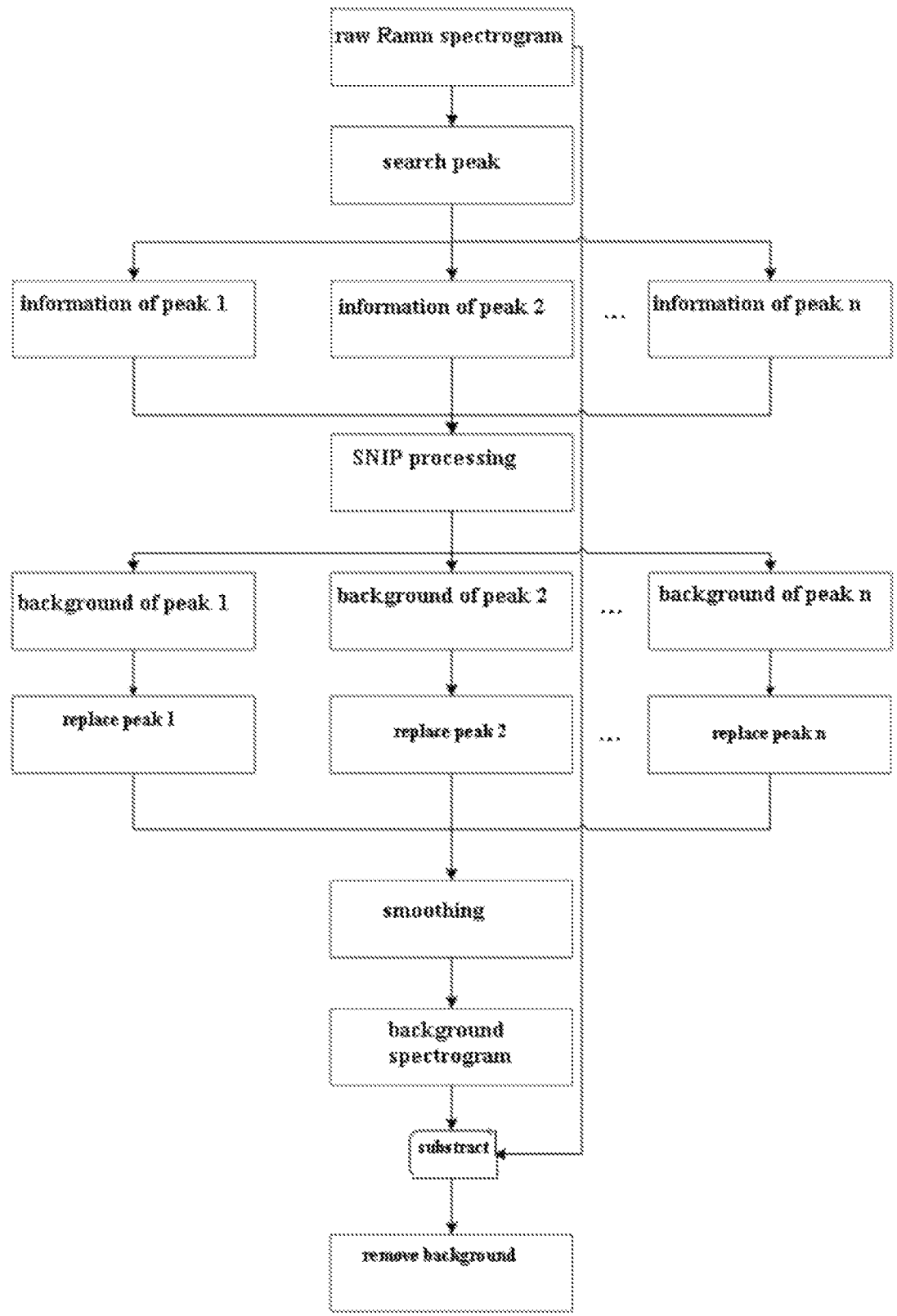
FIG. 3 is a flow chart of a method of identifying substances through a Raman spectrogram by using method for removing background from a spectrogram according to an embodiment of the present disclosure.
Figure 4:
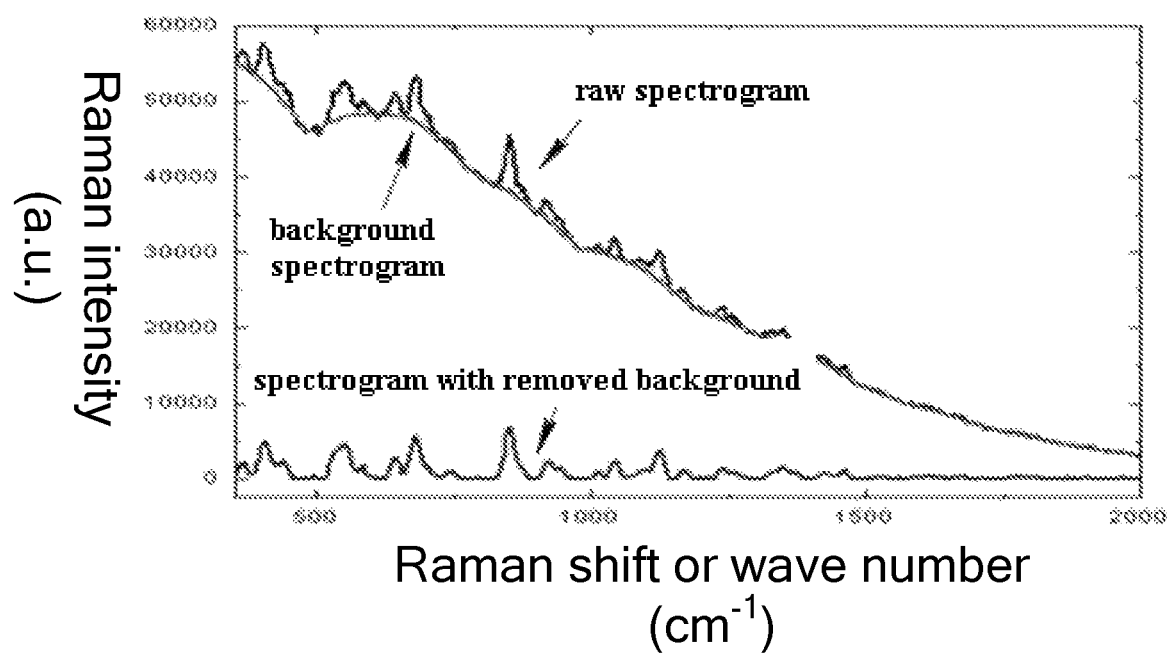
FIG. 4 schematically shows a Raman spectrogram for use in a method for removing background from a spectrogram according to an embodiment of the present disclosure.

In the following, a method for removing background from a spectrogram according to an embodiment of the present disclosure will be described in more detail with reference to FIG. 3 and FIG. 4. FIG. 3 is a flow chart showing removing of background from a Raman spectrogram by using a method of removing background from a spectrogram according to an embodiment of the present disclosure, and FIG. 4 schematically shows a Raman spectrogram for use in a method for removing background from a spectrogram according to an embodiment of the present disclosure. In FIG. 4, the horizontal ordinate represents a Raman shift or wave number (in unit of $cm^{-1}$), and the longitudinal coordinate represents an intensity (which is dimensionless or represented by a.u.).

As shown in FIG. 3 and FIG. 4, a raw Raman spectrogram often includes a plurality of peaks, which may be referred to, for example, as peak 1, peak 2, peak n, and correspondingly, each peak includes respective peak information, particularly, the peaks each have respective peak widths, which may be denoted by $w_1, w_2, \ldots w_n$.

As shown in FIG. 3, each of the peaks (i.e., peak 1, peak 2, ... peak n) is processed by using a SNIP method, and particularly, since peak widths w of respective peaks are different from each other and m=(w−1)/2, the number of iteration m also varies when performing the SNIP processing.

Further, as shown in FIG. 3, within each peak area, data of the raw spectrogram are replaced with the background data obtained through processing by using the SNIP method, so that a background spectrogram is formed in a fitting way, and then the formed background spectrogram is smoothed, the smoothed background spectrogram is shown in FIG. 4. Finally, the smoothed background spectrogram is subtracted from the raw spectrogram so as to obtain a spectrogram with removed background, which is shown in FIG. 4.

As can be seen from FIG. 4, with method for removing background from a spectrogram according to embodiments of the present disclosure, the background can be removed adaptively; further, by using a segmented SNIP method while setting the number of iterations to be (w−1)/2, the background can be fitted as much as possible, the peak shape is maintained, and the calculation speed is improved, thereby facilitating subsequent processing of the spectrogram, and identification and quantitative analysis of a mixture.

Figure 5:
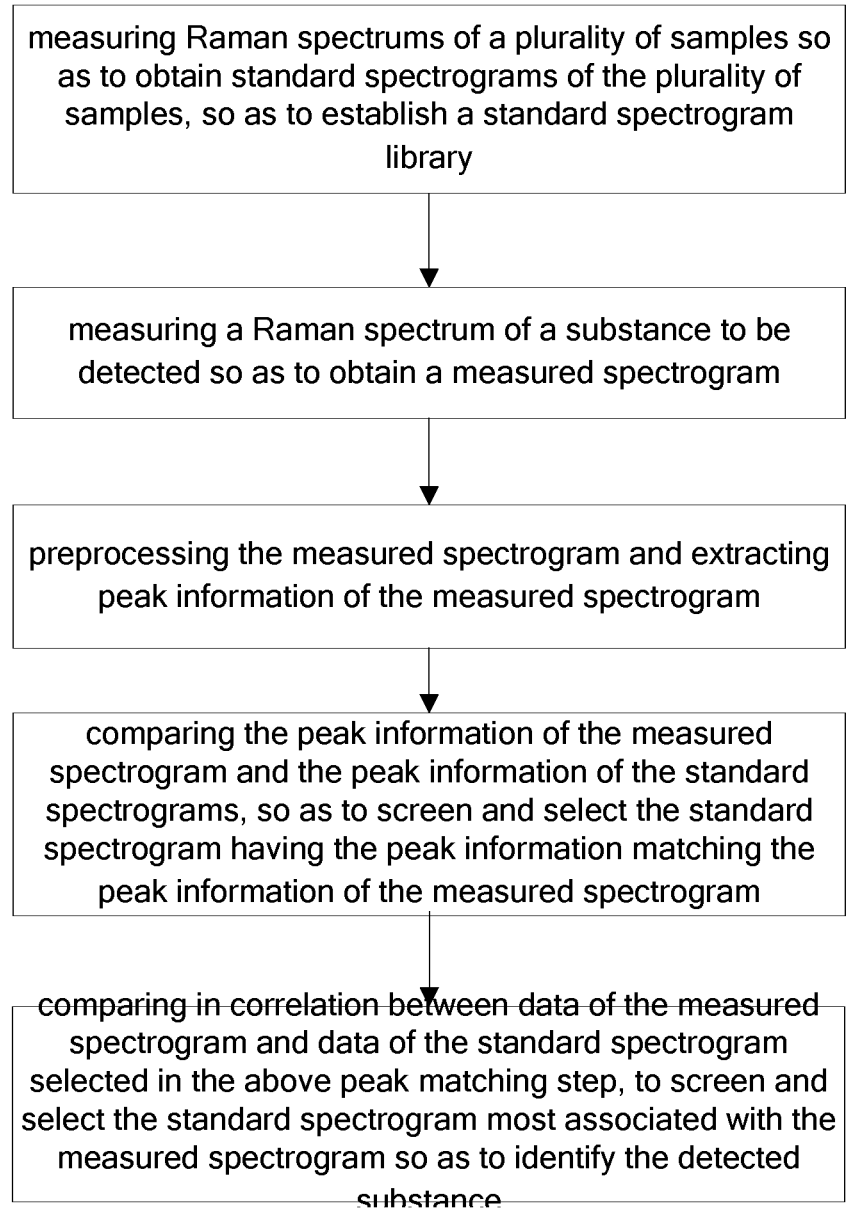
FIG. 5 is a flow chart of a method of identifying substances through a Raman spectrogram by using method for removing background from a spectrogram.

According to some embodiments of the present disclosure, the above method for removing a background from a spectrogram may be applied in a method of identifying substances through a Raman spectrogram, so as to improve speed and accuracy of identifying substances. Hereinafter, a method of identifying substances through a Raman spectrogram according to an embodiment of the present disclosure will be described in detail with reference to FIG. 5. The method may comprise following steps:

a standard spectrogram library establishing step: measuring Raman spectrums of a plurality of samples so as to obtain standard spectrograms of the plurality of samples, preprocessing the standard spectrograms and extracting peak information of the standard spectrograms including peak intensities, peak positions, peak areas and peak widths, and storing the pre-processed standard spectrograms and the extracted peak information into a data base so as to establish a standard spectrogram library;

a measured spectrogram obtaining step: measuring a Raman spectrum of a substance to be detected so as to obtain a measured spectrogram;

a measured spectrogram preprocessing and peak information extracting step: preprocessing the measured spectrogram and extracting peak information of the measured spectrogram, the peak information including a peak intensity, a peak position, a peak area and a peak width of the measured spectrogram;

a peak matching step: comparing the peak information of the measured spectrogram and the peak information of the standard spectrograms, so as to screen and select the standard spectrogram having the peak information matching the peak information of the measured spectrogram; and an identification step: comparing in correlation between data of the measured spectrogram and data of the standard spectrogram selected in the above peak matching step, to screen and select the standard spectrogram most associated with the measured spectrogram so as to identify the detected substance.

In some embodiments, the preprocessing the measured spectrogram in the measured spectrogram preprocessing and peak information extracting step comprises: removing background from the measured spectrogram by using the method of removing background from a spectrogram described in any one of the above embodiments.

In some embodiments, the preprocessing the standard spectrograms in the standard spectrogram library establishing step comprises: removing background from the standard spectrograms by using the method of removing background from a spectrogram described in any one of the above embodiments.

Figure 6:
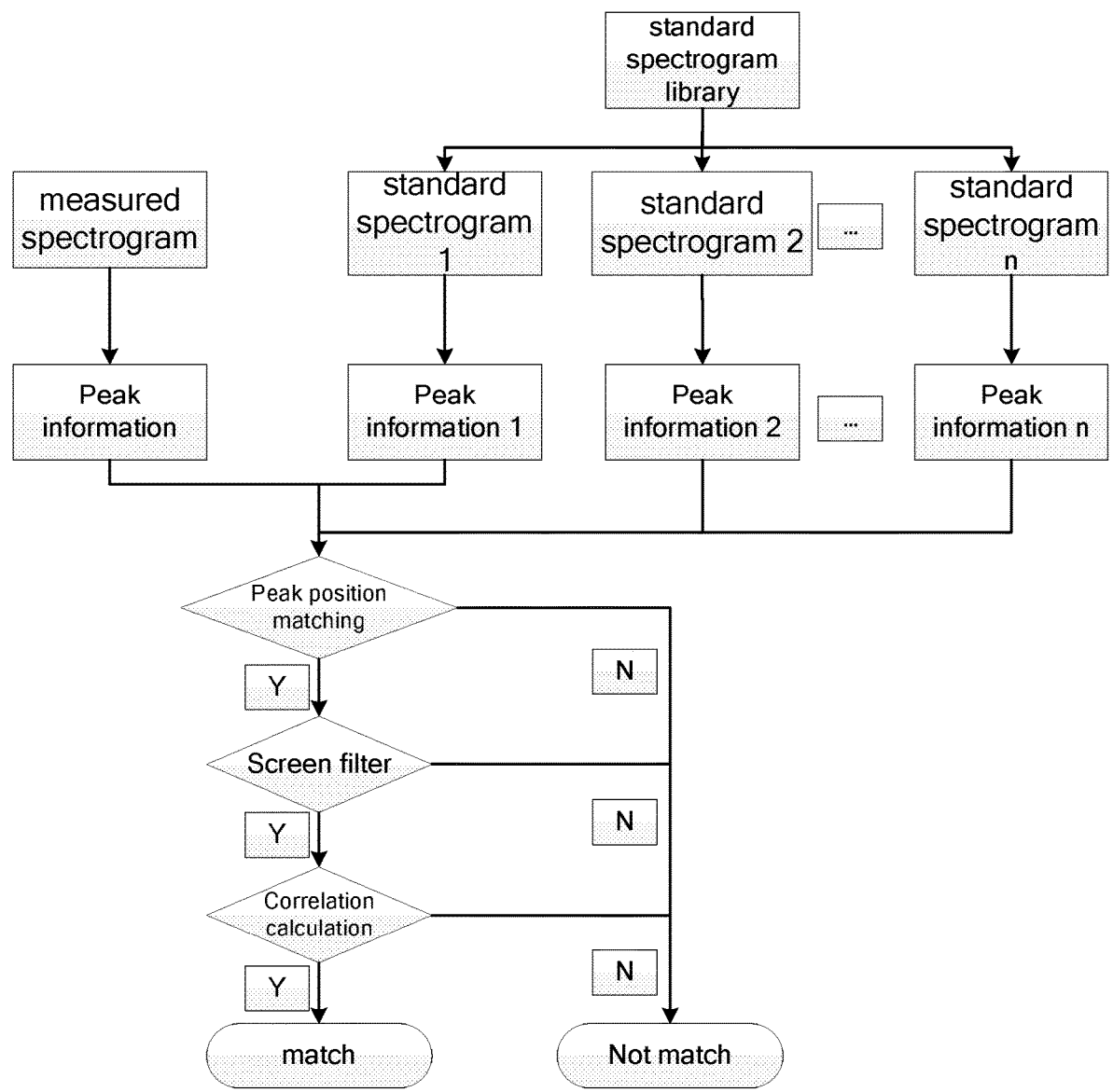
FIG. 6 is a flow chart showing a method of identifying and matching a measured spectrogram to standard spectrograms by using the method of embodiments of the present disclosure.

Specifically, as shown in FIG. 6, pre-processed standard spectrograms, such as a standard spectrogram 1, a standard spectrogram 2, a standard spectrogram n, and correspondingly, extracted peak information of the standard spectrograms, such as peak information 1, peak information 2, peak information n, are stored in the standard spectrogram library. As such, according to an embodiment of the present disclosure, as shown in FIG. 6, the peak matching step may further comprise "peak position matching" step, which may include following steps:

an ordering step: an ordering step: ordering, with the greatest in front in accordance with peak intensities, peaks of the measured spectrogram and peaks of the standard spectrograms respectively, so as to select ordered first N peaks of the measured spectrogram and the standard spectrograms; and a first matching step: comparing peak position information of the ordered first N peaks of the measured spectrogram and the standard spectrograms, so as to screen and select the standard spectrogram having the peak information matching the peak information of the measured spectrogram.

According to a further embodiment of the present disclosure, the first matching step may specifically comprise:

calculating absolute differences between peak positions of ordered first N peaks in accordance with the following formula (1); and determining that the peak information of the measured spectrogram matches the peak information of the standard spectrogram when the calculated absolute differences between the peak positions meets the following condition (1); and determining that the peak information of the measured spectrogram does not match the peak information of the standard spectrogram when the calculated absolute differences between the peak positions do not meet the following condition (1), wherein:

the formula (1) is: $pD=|p2[j].fPos-p1[i].fPos|$, the condition (1) is: $pD<p2[j].fWidth/3$ and $pD<p1[i].fWidth/3$, where, N is a predetermined number of compared peaks, N is a natural number greater than or equal to three;

i, j respectively represent order numbers of the ordered peaks of the standard spectrogram and the measured spectrogram, i and j are each an integer greater than or equal to zero and less than or equal to N;

$p1[i].fPos$ represents a peak position of the $i^{th}$ peak ordered in the standard spectrogram;

$p2[j].fPos$ represents a peak position of the $j^{th}$ peak ordered in the measured spectrogram;

$p1[i].fWidth$ represents a peak width of the $i^{th}$ peak ordered in the standard spectrogram;

$p2[j].fWidth$ represents a peak width of the $j^{th}$ peak ordered in the measured spectrogram; and pD represents an absolute difference between peak positions.

In an embodiment, N is a natural number greater than or equal to three and less than or equal to five. If the value of N is less, for example, less than 3, the number of compared peaks is too small, which is not in favor of screening and selecting the standard spectrogram matching the measured spectrogram, that is, is not in favor of improving validity for identification; If the value of N is too large, the amount of calculation for comparing the peak information will be increased, which will adversely affect a calculation speed of comparing the peak information. If the value of N is a natural number greater than or equal to three and less than or equal to five, requirements for both of the validity for identification achieved by using the peak information and the calculation speed could be met.

Further, as shown in FIG. 6, the peak matching step may further comprise a "screen filter" step, which may specifically include:

a peak matching weight calculation step: establishing a penalty function in accordance with the following formula (2) so as to calculate a peak matching weight; and a second matching step: determining that the peak information of the measured spectrogram matches the peak information of the standard spectrogram when the peak matching weight is greater than or equal to a preset weight threshold; and determining that the peak information of the measured spectrogram does not match the peak information of the standard spectrogram when the peak matching weight is less than or equal to the preset weight threshold, wherein, the formula (2) is:

$h=(1-2*|j-i|/10)*(0.5/(i+1))*\exp(-pD*2/\min(p1[i].fWidth,p2[j].fWidth))$, where, h represents the peak matching weight;

"min(p1[i].fWidth,p2[j].fWidth)" represents a less one of the p1[i].fWidth and the p2[j].fWidth; and "exp" represents a power function with a base of natural logarithm of e.

In embodiments of the present disclosure, the peak matching weight calculation step and the second matching step are performed when determining that the peak information of the measured spectrogram matches the peak information of the standard spectrogram in the first matching step. In order words, in embodiments of the present disclosure, the calculation based on the penalty function and the comparing of peak matching weights will be performed only when it is determined in the first matching step that the absolute differences of the peaks meet requirements. Similarly, since the amount of calculation for the absolute differences of the peaks is less than the amount of calculation for the penalty function, a preliminary screening operation will be preformed through the calculation of the absolute differences of the peaks before the calculation of the penalty function, so that the amount of calculation can be greatly reduced, thereby improving speed and accuracy of identification.

According to an embodiment of the present disclosure, the step of comparing data of the measured spectrogram and data of the prestored standard spectrogram may include: comparing in correlation between data of the measured spectrogram and data of the prestored standard spectrogram, that is, a "correlation calculation" step shown in FIG. 6.

In an embodiment, the step of comparing in correlation between data of the measured spectrogram and data of the prestored standard spectrogram comprises:

calculating a correlation coefficient between the data of the measured spectrogram and the data of the prestored standard spectrogram, determining the measured spectrogram matches standard spectrogram when the calculated correlation coefficient is greater than or equal to a preset correlation threshold; and determining the measured spectrogram does not match standard spectrogram when the calculated correlation coefficient is less than the preset correlation threshold.

Specifically, the correlation coefficient is a parameter for studying a linear correlation between variables and is used for determining a relationship between vectors. For example, there are feature vectors X (x1, x2, . . . , xn) and Y (y1, y2, . . . , yn), and a correlation coefficient r between them may be defined as follows:

$$r = \frac{\sum_{i=1}^{n}(x_i - \bar{x})(y_i - \bar{y})}{\sqrt{\sum_{i=1}^{n}(x_i - \bar{x})^2 \cdot \sum_{i=1}^{n}(y_i - \bar{y})^2}}$$

where, $\bar{x}$ and $\bar{y}$ represent mean values of the vectors X and Y respectively, and i represents the $i^{th}$ datum of the vector.

According to an embodiment of the present disclosure, the step of comparing in correlation between data of the measured spectrogram and data of the prestored standard spectrogram is performed within a union interval of peak areas of all of peaks of the measured spectrogram and the standard spectrogram. That is, the step of comparing in correlation between data of the measured spectrogram and data of the prestored standard spectrogram is not performed within the whole interval of the spectrogram, rather, is performed within a union interval of peak areas of all of peaks of the measured spectrogram and the standard spectrogram. The "union interval of peak areas of all of peaks of the measured spectrogram and the standard spectrogram" herein represents an interval consisted of peak areas of all of peaks of the measured spectrogram and the standard spectrogram. As such, the amount of data that needs to be compared for correlation can be further reduced, thereby further increasing the operation speed and ensuring the accuracy of the calculation.

In embodiments of the present disclosure, the measured spectrogram and the standard spectrograms are initially screened by comparing a local feature (the "peak"), by using the peak information of the spectrograms. After the initial screening, the global comparison of data of the spectrograms is performed. This can not only greatly shorten the matching and identifying time, but also improve the accuracy of matching and identifying. Moreover, in the "peak position matching" and "screen filter" steps shown FIG. 6, if it is determined that the peak information of the measured spectrogram does not match the peak information of the standard spectrogram, the matching process is terminated immediately without the need for a subsequent matching and identifying process, which can greatly improve the calculation speed when determining the mismatch therebetween. The test proves that the matching and identifying time is shortened to be about 5% of a conventional method, and the accuracy of the matching recognition is improved by 10%.

Figure 7:
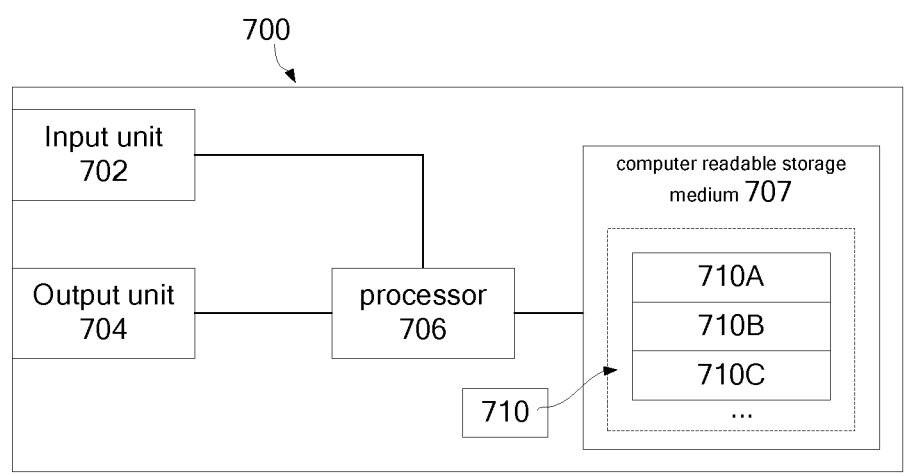
FIG. 7 is a block diagram showing an example hardware arrangement of an electronic apparatus for executing the method of embodiments of the present disclosure.

According to a further embodiment of the present disclosure, an electronic apparatus is also provided, and FIG. 7 is a block diagram showing an exemplary hardware arrangement of the electronic apparatus 700. The electronic apparatus 700 includes a processor 706 (for example, a microprocessor (µP), a signal processor (DSP), etc.). The processor 706 may be a single processing unit or a plurality of processing units for performing the different actions of the method steps described herein. Electronic apparatus 700 may also include an input unit 702 for receiving signals from other entities and an output unit 704 for providing signals to other entities. The input unit 702 and the output unit 704 may be arranged as a single entity or as separate entities.

Furthermore, the electronic apparatus 700 may include at least one computer readable storage medium 707 having a non-volatile or volatile storage form, for example, an electrically erasable programmable read-only storage (EEPROM), a Flash memory and/or a hard disk. The computer readable storage medium 707 includes a computer program 710 including codes/computer readable instructions that, when executed by the processor 706 in the electronic apparatus 700, enable the electronic apparatus 700 to perform the above process described in conjunction with the above embodiments and any variations thereof.

The computer program 710 may be configured as computer program codes having architectures such as computer program modules 710A-710C. The computer program modules can substantially perform various actions in the processes described in the above embodiments to simulate a device. In other words, when different computer program modules are implemented in the processor 706, they may correspond to the above different units in the apparatus.

Although the code means in the embodiment disclosed in connection with FIG. 7 is implemented as a computer program module, and enable, when executed in the processor 706, the electronic apparatus 700 to perform the actions described above in connection with the above embodiments, in the alternative embodiment, at least one of the code means can be implemented at least partially as a hardware circuit.

The processor may be a single CPU (Central Processing Unit), or may also include two or more processing units. For example the processor may include a general purpose microprocessor, an instruction set processor and/or a related chipset and/or a dedicated microprocessor (for example, an application specific integrated circuit (ASIC)). The processor may also include an onboard storage for caching purposes. The computer program may be carried by a computer program product connected to the processor. The computer program product may include a computer readable medium having a computer program stored thereon. For example, the computer program product may be a flash memory, a random access storage (RAM), a read only storage (ROM) or EEPROM, and in an alternative embodiment, the above computer program modules may be distributed in the form of storages in different computer program products.

It should be understood by those skilled in the art that in some embodiments of the present disclosures, although the Raman spectrogram is used as an example to illustrate the technical concept of the present disclosure, the present disclosure is not limited to the analysis and processing of the Raman spectrogram.

Although the present disclosure has been described in conjunction with the accompanying drawings, the embodiments disclosed in the accompanying drawings are intended to exemplify the preferred embodiment of the present disclosure, and shall not be construed as a limitation on the present disclosure.

Although some embodiments of the present disclosure have been shown and described, those skilled in the art will appreciate that changes can be made to these embodiments without departing from the principles and spirit of the present general inventive concept. The scope of the present disclosure is defined by the claims and their equivalents.

What is claimed is:

1. A method of identifying substances through a Raman spectrogram, comprising:

a standard spectrogram library establishing step: measuring Raman spectrums of a plurality of samples so as to obtain standard spectrograms of the plurality of samples, preprocessing the standard spectrograms and extracting peak information of the standard spectrograms including peak intensities, peak positions, peak areas and peak widths, and storing the preprocessed standard spectrograms and the extracted peak information into a data base so as to establish a standard spectrogram library;

a measured spectrogram obtaining step: measuring a Raman spectrum of a substance to be detected so as to obtain a measured spectrogram;

a measured spectrogram preprocessing and peak information extracting step: preprocessing the measured spectrogram and extracting peak information of the measured spectrogram, the peak information including a peak intensity, a peak position, a peak area and a peak width of the measured spectrogram;

a peak matching step: comparing the peak information of the measured spectrogram and the peak information of the standard spectrograms, so as to screen and select the standard spectrogram having the peak information matching the peak information of the measured spectrogram; and an identification step: comparing in correlation between data of the measured spectrogram and data of the standard spectrogram selected in the peak matching step, to screen and select the standard spectrogram most associated with the measured spectrogram so as to identify the detected substance, wherein, the preprocessing the measured spectrogram in the measured spectrogram preprocessing and peak information extracting step comprises: removing background from the measured spectrogram by:

finding out peak information of a raw spectrogram, the peak information including a peak position, a starting point, an ending point, and a peak width of a peak;

processing, within each peak area defined by the starting point and the ending point of each peak of the raw spectrogram, the each peak of the raw spectrogram by using a Statistics-sensitive Nonlinear Iterative Peak-clipping (SNIP) method so as to obtain background data within each peak area;

replacing, within each peak area, data of the raw spectrogram with the background data obtained through the processing by using the SNIP method, so as to form a background spectrogram in a fitting way;

smoothing the formed background spectrogram; and subtracting the smoothed background spectrogram from the raw spectrogram so as to obtain a spectrogram with removed background.

2. The method according to claim 1, wherein, the preprocessing the standard spectrograms in the standard spectrogram library establishing step comprises: removing background from the standard spectrograms by the following:

finding out peak information of a standard spectrogram, the peak information including a peak position, a starting point, an ending point, and a peak width of a peak;

processing, within each peak area defined by the starting point and the ending point of each peak of the standard spectrogram, the each peak of the standard spectrogram by using a SNIP method so as to obtain background data within each peak area;

replacing, within each peak area, data of the standard spectrogram with the background data obtained through the processing by using the SNIP method, so as to form a background spectrogram in a fitting way;

smoothing the formed background spectrogram; and subtracting the smoothed background spectrogram from the standard spectrogram.

3. The method according to claim 1 or 2, wherein the peak matching step comprises:

an ordering step: ordering, with the greatest in front in accordance with peak intensities, peaks of the measured spectrogram and peaks of the standard spectrograms respectively, so as to select ordered first N peaks of the measured spectrogram and the standard spectrograms; and a first matching step: comparing peak position information of the ordered first N peaks of the measured spectrogram and the standard spectrograms, so as to screen and select the standard spectrogram having the peak information matching the peak information of the measured spectrogram.

4. The method according to claim 3, wherein the first matching step specifically comprises:

calculating absolute differences between peak positions of ordered first N peaks in accordance with the following formula (1); and determining that the peak information of the measured spectrogram matches the peak information of the standard spectrogram when the calculated absolute differences between the peak positions meets the following condition (1); and determining that the peak information of the measured spectrogram does not match the peak information of the standard spectrogram when the calculated absolute differences between the peak positions do not meet the following condition (1), wherein:

the formula (1) is: $pD=|p2[j].fPos-p1[i].fPos|$, the condition (1) is: $pD<p2[j].fWidth/3$ and $pD<p1[i].fWidth/3$, where, N is a predetermined number of compared peaks, N is a natural number greater than or equal to three;

i,j respectively represent order numbers of the ordered peaks of the standard spectrogram and the measured spectrogram, i and j are each an integer greater than or equal to zero and less than or equal to N;

$p1[i].fPos$ represents a peak position of the $i^{th}$ peak ordered in the standard spectrogram;

$p2[j].fPos$ represents a peak position of the $j^{th}$ peak ordered in the measured spectrogram;

$p1[i].fWidth$ represents a peak width of the $i^{th}$ peak ordered in the standard spectrogram;

$p2[j].fWidth$ represents a peak width of the $j^{th}$ peak ordered in the measured spectrogram; and pD represents an absolute difference between peak positions.

5. The method according to claim 4, wherein the peak matching step further comprises:

a peak matching weight calculation step: establishing a penalty function in accordance with the following formula (2) so as to calculate a peak matching weight; and a second matching step: determining that the peak information of the measured spectrogram matches the peak information of the standard spectrogram when the peak matching weight is greater than or equal to a preset weight threshold; and determining that the peak information of the measured spectrogram does not match the peak information of the standard spectrogram when the peak matching weight is less than or equal to the preset weight threshold, wherein, the formula (2) is:

$$h=(1-2*|j-i|/10)*(0.5/(i+1))*\exp(-pD*2/\min(p1[i].fWidth,p2[j].f$$

where, h represents the peak matching weight.

6. The method according to claim 5, wherein the peak matching weight calculation step and the second matching step are performed when determining that the peak information of the measured spectrogram matches the peak information of the standard spectrogram in the first matching step.

7. The method according to claim 3, wherein, N is a natural number greater than or equal to three and less than or equal to five.

8. The method according to claim 3, wherein, within a union interval of peak areas of all of peaks of the measured spectrogram and the standard spectrogram, the step of comparing in correlation between data of the measured spectrogram and data of the standard spectrogram selected in the peak matching step is performed.

9. An electronic apparatus, comprising:

a storage for storing executable instructions therein; and a processor configured to execute the executable instructions stored in the storage to perform the method of claim 4.

10. The method according to claim 1, wherein the step of obtaining background data within each peak area comprises:

transforming, within each peak area, an intensity value corresponding to each wave number within the peak area by using a transformation formula, the transformation formula being: $v(i)=\ln[\ln(\sqrt{y(i)+1}+1)+1]$;

performing iteration calculation based on a SNIP formula so as to successively calculate $v_1(i)$, $v_2(i)$, unit $v_m(i)$, the SNIP formula being: $v_p(i)=\min\{v_{p-1}(i),[v_{p-1}(i+p)+v_{p-1}(i-p)]/2\}$; and performing, after calculating $v_m(i)$, an inverse operation based on the above transformation formula to calculate $y(i)$ corresponding to $v_m(i)$ so as to obtain the background data within the peak area, wherein, i is a wave number of the raw spectrogram, $y(i)$ is an intensity value corresponding to the $i^{th}$ wave number of the raw spectrogram, and $v(i)$ is an operation result of $y(i)$;

wherein m is a predetermined number of iterations, p is a current number of iterations, $1<p\leq m$, $v_p(i)$ represents $v(i)$ calculated through the $p^{th}$ iteration, $v_{p-1}(i)$, $v_{p-1}(i+p)$ and $v_{p-1}(i-p)$ respectively represent $v(i)$, $v(i+p)$ and $v(i-p)$ calculated through the $(p-1)^{th}$ iteration, and $v(i+p)$ and $v(i-p)$ respectively represent operation results of intensity values corresponding to the $(i+p)^{th}$ wave number and the $(i-p)^{th}$ wave number.

11. The method according to claim 10, wherein for each peak area, the predetermined number of iterations m meets a following relation:

$m=(w-1)/2$, where w is the peak width of the peak area.

* * * * *